(12) United States Patent
Ikeuchi et al.

(10) Patent No.: US 7,985,251 B2
(45) Date of Patent: *Jul. 26, 2011

(54) STENT

(75) Inventors: Ken Ikeuchi, Kyoto (JP); Kouji Mori, Kyoto (JP); Hiroo Iwata, Kyoto (JP); Kazuaki Mitsudou, Okayama (JP); Hiroaki Nomiyama, Oita (JP); Yoshiharu Yoshikawa, Oita (JP); Masatoshi Watanabe, Oita (JP); Shuzou Yamashita, Tokyo (JP); Kazunori Murakami, Oita (JP)

(73) Assignees: Kawasumi Laboratories, Inc., Tokyo (JP); Kazuaki Mitsudou, Kurashiki-shi (JP); Ken Ikeuchi, Kyoto-shi (JP); Kouji Mori, Kyoro-shi (JP); Hiroo Iwata, Kyoto-shi (JP)

( * ) Notice: Subject to any disclaimer, the term of this patent is extended or adjusted under 35 U.S.C. 154(b) by 167 days.

This patent is subject to a terminal disclaimer.

(21) Appl. No.: 10/490,736

(22) PCT Filed: Oct. 16, 2002

(86) PCT No.: PCT/JP02/10705
§ 371 (c)(1),
(2), (4) Date: Sep. 15, 2004

(87) PCT Pub. No.: WO03/039642
PCT Pub. Date: May 15, 2003

(65) Prior Publication Data
US 2005/0015136 A1  Jan. 20, 2005

(30) Foreign Application Priority Data

Oct. 16, 2001  (JP) ................................. 2001-318098
Oct. 19, 2001  (JP) ................................. 2001-322254

(51) Int. Cl.
A61F 2/06  (2006.01)
(52) U.S. Cl. ........................................................ 623/1.15
(58) Field of Classification Search ................. 623/1.15, 623/1.31, 1.11–1.48
See application file for complete search history.

(56) References Cited

U.S. PATENT DOCUMENTS 5,697,971 A * 12/1997 Fischell et al. ............... 623/1.15
5,911,754 A *  6/1999 Kanesaka et al. ............ 623/1.15

(Continued)

FOREIGN PATENT DOCUMENTS

JP  11-505441  5/1999

(Continued)

*Primary Examiner* — Elizabeth Houston
(74) *Attorney, Agent, or Firm* — Oblon, Spivak, McClelland, Maier & Neustadt, L.L.P.

(57) ABSTRACT

A stent having a generally tubular body formed of ring units formed of a plurality of cells each and expandable in the radial direction, wherein each ring unit is constituted of cells connected to one another above and below, arranged to surround the center line of the stent, the ring units are arranged in the axial direction of the stent, and are connected with connector portions, each connector portion is formed of curved portions each having an arch and a generally linear portion continued thereto, 3 to 8 cells are arranged in the axial direction per 10 mm of the length of the stent, and the ratio of the length of the cell in the axial direction and the length of the connector portion is determined such that on the basis that when the length of the cell is 100, that of the connector portion 50 to 100, thereby securing flexibility and radial sustaining force.

4 Claims, 12 Drawing Sheets

U.S. PATENT DOCUMENTS

| | | | |
|---|---|---|---|
| 5,913,895 A * | 6/1999 | Burpee et al. | 623/1.2 |
| 5,922,021 A * | 7/1999 | Jang | 623/1.15 |
| 6,039,756 A * | 3/2000 | Jang | 623/1.15 |
| 6,113,627 A * | 9/2000 | Jang | 623/1.5 |
| 6,129,754 A * | 10/2000 | Kanesaka et al. | 623/1.15 |
| 6,190,403 B1 * | 2/2001 | Fischell et al. | 623/1.16 |
| 6,200,334 B1 * | 3/2001 | Jang | 623/1.15 |
| 6,669,722 B2 * | 12/2003 | Chen et al. | 623/1.15 |
| 6,749,629 B1 * | 6/2004 | Hong et al. | 623/1.15 |
| 2002/0123798 A1 * | 9/2002 | Burgermeister | 623/1.17 |

FOREIGN PATENT DOCUMENTS

| | | |
|---|---|---|
| JP | 2000-42119 | 2/2000 |
| WO | 99/38457 | 8/1999 |

* cited by examiner (A)  (B)

STENT

TECHNICAL FIELD

The present invention relates to improvements in a stent used for amelioration of a stenosed portion that occurs in an organism such as a blood vessel.

TECHNICAL BACKGROUND

A stent refers to a tubular medical tool that is placed in a stenosed portion or the like for dilating the stenosed portion, etc., to secure a necessary lumen region when a blood vessel or a lumen in an organism is stenosed or occluded. The stent is inserted into a body with its diameter kept small, and is expanded in a stenosed portion, etc., to have a larger diameter so that the above lumen is dilated and sustained.

Conventional stents are typically as shown in FIGS. 11 and 12. However, these have had the following drawbacks. FIG. 11A and FIG. 12A show stents before expansion, and FIG. 11B and FIG. 12B show the stents after expansion.

In a stent 201 shown in FIG. 11, cells 206 constituting a ring unit 204 have a structure in which three linear portions 207 are connected in parallel and a curved portion 206A between the cells 206 is arranged so as to face a space 206B in the vicinity of cells 206 constituting another ring unit 204. Having the above structure, the above stent is excellent in proper radial sustaining force (which, in a general expression, means a force to sustain an expansion state of the stent against an external force from and through a blood vessel wall when the stent is expanded to be fixed to the vessel wall) and flexibility. Since, however, the stent is inserted through tortuous parts of a blood vessel, along the curves of it, during expansion or delivery, the cells 206 partly project outward to be caught by the wall of the vessel, so that the delivery has been sometimes difficult (which will be referred to as "flare phenomenon" hereinafter).

In a stent 241 shown in FIG. 12, cells 246 which constitute a ring unit have a structure in which generally-<-shaped struts (linear bodies) 247 are connected with a connector portion 245. Therefore, the stent 241 has advantages that it has a strong radial-sustaining force and that the above generally-<-shaped struts 247 are not warped outward during expansion or insertion through a tortuous blood vessel. However, the defect with it is that it lacks flexibility. It is considered that the above problem is caused since each connector portion 245 has only one curved portion and also since the connector portion 245 is of small length.

The conventional stents thus have the problem that they are not well-balanced in flexibility and radial sustaining force.

The present inventors have made diligent studies for overcoming the above problems in order to provide a new stent having both flexibility and radial sustaining force, and have arrived at the present invention.

DISCLOSURE OF THE INVENTION

The present invention has been made from the above viewpoint, and according to the present invention, there is provided an invention of the following subject matters.

[1] A stent (1, 1A, 1B) with high bending flexibility, which has a generally tubular body formed of ring units formed of a plurality of cells each, and said tubular body is expandable in the radius direction of said tubular body from inside of said tubular body, each ring unit (4, 4A, 4B) being constituted of said plurality of cells (6, 6A, 6B) connected to one another above and below and arranged so as to surround the center line (C1) of the stent (1, 1A, 1B) forming said tubular body, a plurality of said ring units (4, 4A, 4B) being arranged in the axial direction of the stent (1, 1A, 1B) forming said tubular body, adjacent ring units (4, 4A, 4B) having at least one site each through which the adjacent ring units (4, 4A, 4B) are connected to each other with one of connector portions (5, 5A, 5B), each of said connector portions (5, 5A, 5B) being formed of curved portions (8, 8A, 8B) having at least 2 arches and a generally linear portion (7, 7A, 7B) continued to, and from, said curved portions (8, 8A, 8B), wherein said cells (6, 6A, 6B) are so arranged in the axial direction of the stent that, 3 to 8 cells being disposed per 10 mm of the length of said stent (1, 1A, 1B), and the ratio of the length (6L, 6AL, 6BL) of said cell (6, 6A, 6B) in the axial direction of the stent and the length (5L, 5AL, 5BL) of said connector portion (5, 5A, 5B) in the axial direction of the stent is determined such that on the basis that when the length (6L, 6AL, 6BL) of said cell (6, 6A, 6B) in the axial direction of the stent is taken as 100, the length (5L, 5AL, 5BL) of said connector portion (5, 5A, 5B) in the axial direction of the stent is 50 to 100.

[2] A stent (1, 1A, 1B) with high radial force and bending flexibility, which has a generally tubular body formed of ring units formed of a plurality of cells each and is expandable in the radius direction of said tubular body from inside of said tubular body, each ring unit (4, 4A, 4B) being constituted of said plurality of cells (6, 6A, 6B) connected to one another above and below and arranged so as to surround the center line (C1) of the stent (1, 1A, 1B) forming said tubular body, a plurality of said ring units being arranged in the axial direction of the stent (1, 1A, 1B) forming said tubular body, adjacent ring units (4, 4A, 4B) having at least one site each through which the adjacent ring units (4, 4A, 4B) are connected to each other with one of connector portions (5, 5A, 5B), each of said connector portions (5, 5A, 5B) being formed of curved portions (8, 8A, 8B) having at least 2 arches and a generally linear portion (7, 7A, 7B) continued to, and from, said curved portions (8, 8A, 8B), (i) wherein each of said cells (6, 6A, 6B) has at least one curved portion (12, 12A, 12B) and has a generally linear portion (11, 11A, 11B) and a generally linear line portion (15, 15A, 13B) which are adjacent to said curved portion (12, 12A, 12B), when the stent is expanded until said tubular body has a diameter (φ) of 2.5 mm, the generally linear portion (11, 11A, 11B) and the generally linear portion (15, 15A, 13B) form an angle (θ) of at least 30° after expansion, and said cells (6, 6A, 6B) are arranged in the radius direction, 6 to 12 cells being arranged when the tubular body has a diameter (φ) of 3.0 mm or more after expansion of the stent (1, 1A, 1B), and (ii) wherein said cells (6, 6A, 6B) are so arranged in the axial direction of the stent that, 3 to 8 cells being disposed per 10 mm of the length of said stent (1, 1A, 1B), and the ratio of the length (6L, 6AL, 6BL) of said cell (6, 6A, 6B) in the axial direction of the stent and the length (5L, 5AL, 5BL) of said connector portion (5, 5A, 5B) in the axial direction of the stent is determined such that on the basis that when the length (6L, 6AL, 6BL) of said cell (6, 6A, 6B) in the axial direction of the stent is taken as 100, the length (5L, 5AL, 5BL) of said connector portion (5, 5A, 5B) in the axial direction of the stent is 50 to 100.

[3] The stent (1, 1A, 1B) as recited in the above [1] or [2], wherein said cells (6, 6A, 6B) have a thickness of 0.06 mm to 0.12 mm and a width of 0.08 mm to 0.15 mm and said connector portions (5, 5A, 5B) have a thickness of 0.06 to 0.12 mm and a width of 0.04 mm to 0.10 mm.

[4] The stent (1, 1A, 1B) as recited in any one of the above [1] to [3], wherein the connector portions (5, 5A, 5B) at the outermost ends of said stent 1, 1A, 1B) have a larger length or a smaller width than the connector portions (5, 5A, 5B) on the inward side of the stent 1, 1A, 1B) so that the stent has more flexibility.

[5] A stent 1, 1A, 1B) which has a generally tubular body formed of ring units formed of a plurality of cells each and is expandable outwardly in the radius direction of said tubular body from inside of said tubular body, each ring unit (4, 4A, 4B) being constituted of said plurality of cells (6, 6A, 6B) connected to one another above and below and arranged so as to surround the center line (C1) of the stent 1, 1A, 1B) forming said tubular body, a plurality of said ring units (4, 4A, 4B) being arranged in the axial direction of the stent 1, 1A, 1B) forming said tubular body, adjacent ring units (4, 4A, 4B) having at least one site each through which the adjacent ring units (4, 4A, 4B) are connected to each other with one of connector portions (5, 5A, 5B), each of said connector portions (5, 5A, 5B) being formed of curved portions (8, 8A, 8B) having at least 2 arches and a generally linear portion (7, 7A, 7B) continued to, and from, said curved portions (8, 8A, 8B), wherein said cells (6, 6A, 6B) have a thickness of 0.06 mm to 0.12 mm and a width of 0.08 mm to 0.15 mm, and said connector portions (5, 5A, 5B) have a thickness of 0.06 mm to 0.12 mm and a width of 0.04 mm to 0.10 mm.

[6] The stent (1, 1A, 1B) as recited in the above [5], wherein each of said cells has at least one curved portion (12, 12A, 12B) and has a generally linear portion (11, 11A, 11B) and a generally linear portion (15, 15A, 13B) which are adjacent to said curved portion (12, 12A, 12B), when the stent is expanded until said tubular body has a diameter (φ) of 2.5 mm, the generally linear portion (11, 11A, 11B) and the generally linear portion (15, 15A, 13B) form an angle (θ) of at least 30° after expansion, and said cells (6, 6A, 6B) are so arranged in the radius direction of the stent, that 6 to 12 cells being disposed when the tubular body has a diameter (φ) of 3.0 mm or more after expansion of the stent (1, 1A, 1B).

[7] The stent 1, 1A, 1B) with high bending flexibility as recited in the [5] or [6], wherein the ratio of the length (6L, 6AL, 6BL) of said cell (6, 6A, 6B) in the axial direction of the stent and the length (5L, 5AL, 5BL) of said connector portion (5, 5A, 5B) in the axial direction of the stent is determined such that on the basis that when the length (6L, 6AL, 6BL) of said cell (6, 6A, 6B) in the axial direction of the stent is taken as 100, the length (5L, 5AL, 5BL) of said connector portion (5, 5A, 5B) in the axial direction of the stent is 50 to 100.

Figure 1:
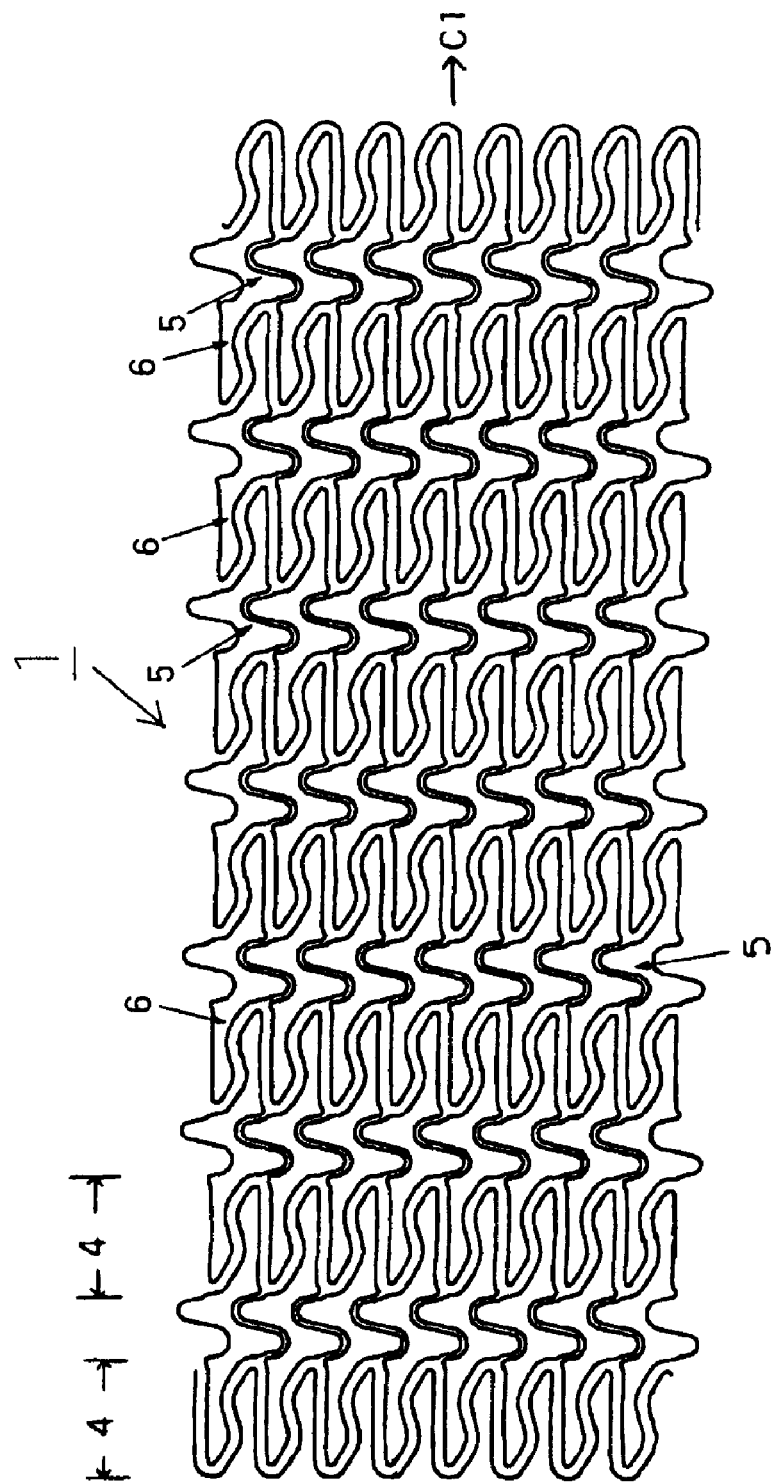
FIG. 1 is a plan view of a stent of the present invention.

In the drawings, 1, 1A and 1B indicate stents, 4, 4A and 4B indicate ring units, 5, 5A and 5B indicate connector portions, 6, 6A and 6B indicate cells, 7 indicates a generally linear portion, 8, 8A and 8B indicate curved portions of connector portions, 9 indicates a connection portion, 11, 11A and 13B indicate generally linear portions, 12, 12A and 12B indicate curved portions of cells, 13 and 13A indicate curved line portion of cells, 14 and 14A indicate minor curved portions of cells, 15 and 15A indicate generally linear portions of cells, 17 indicates a generally-<-shaped cell, 18 indicates a generally-S-shaped connection portion, and 19 indicates a component portion in stents A and B.

PREFERRED EMBODIMENTS OF THE INVENTION

The present invention will be explained in detail with reference to the drawings hereinafter.

Figure 2:
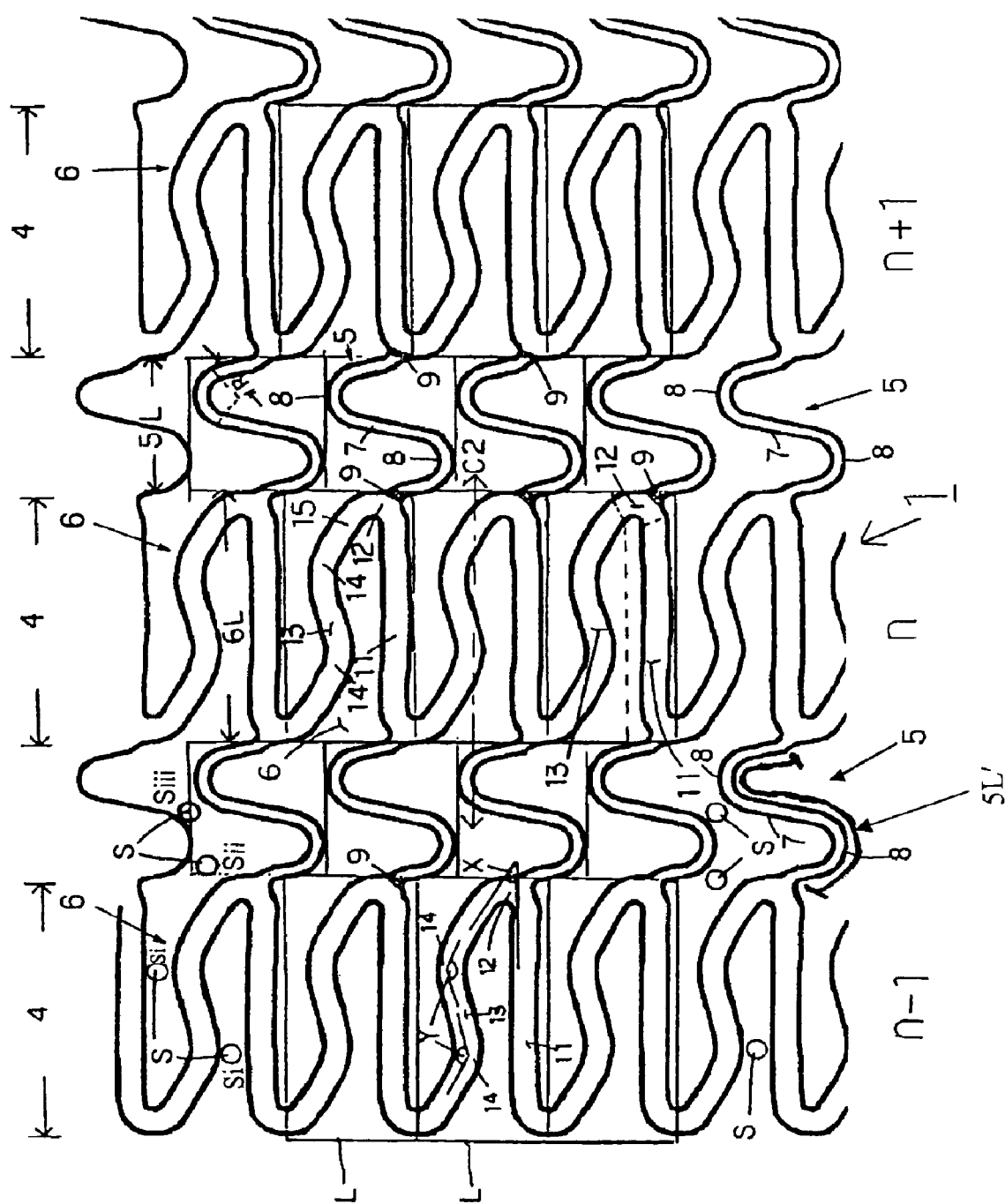
FIG. 2 is an enlarged view of FIG. 1.
Figure 3:
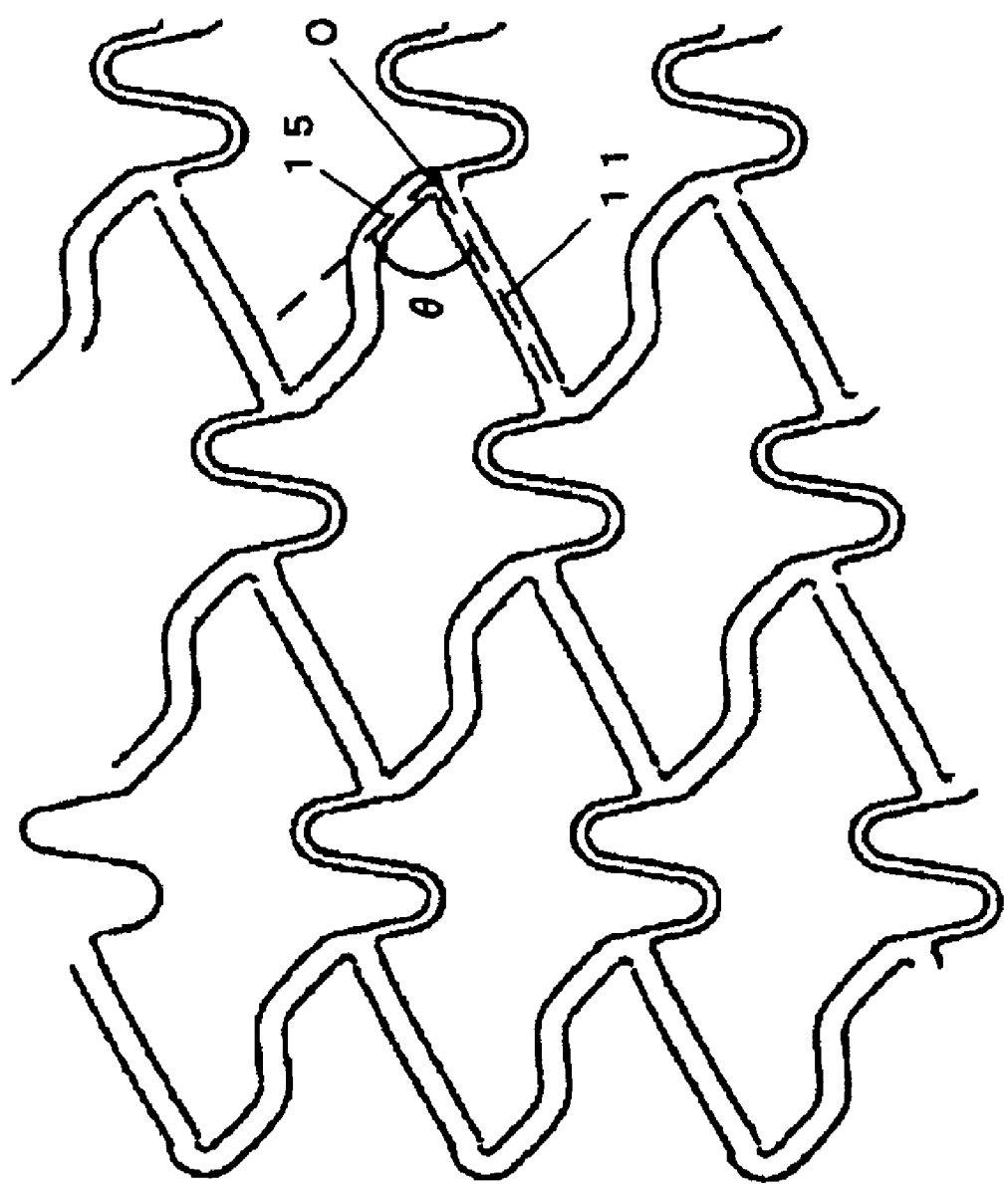
FIG. 3 is an enlarged view showing a state of the present invention after expansion.
Figure 4:
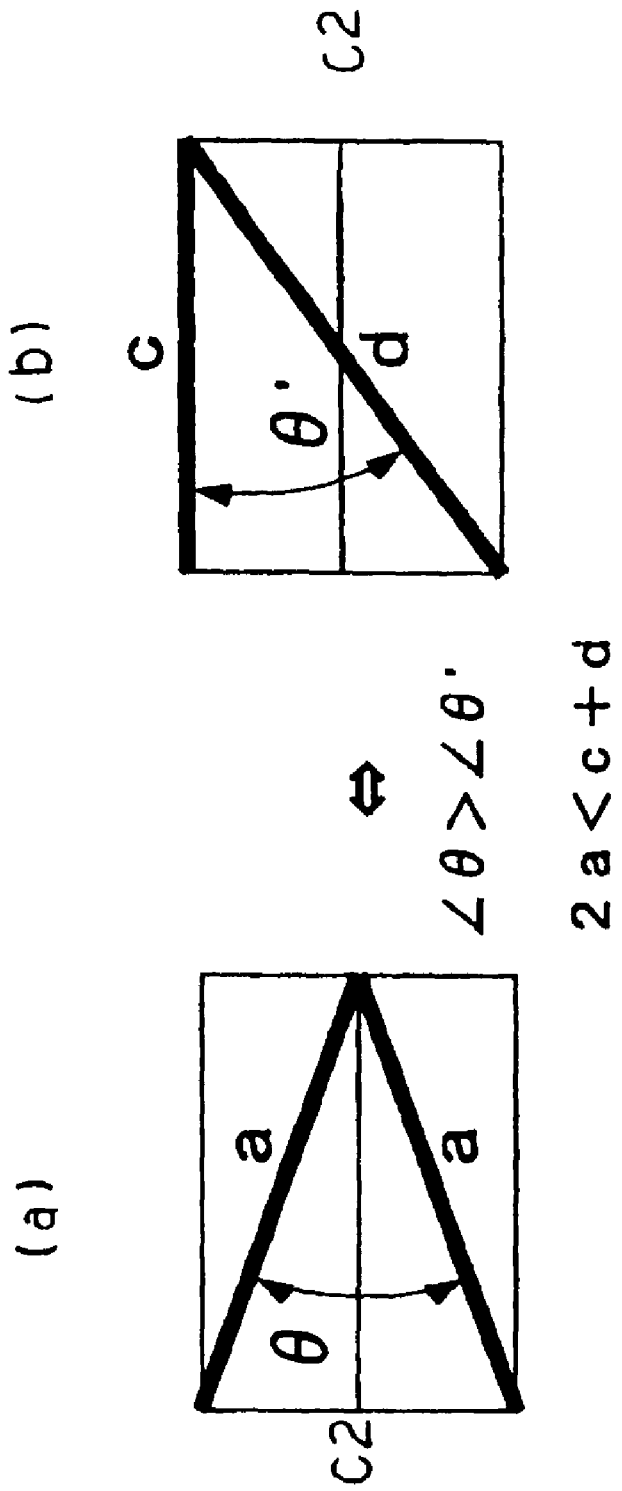
FIG. 4 shows conceptual views of struts constituting a cell.

FIG. 1 is a plan view of the stent of the present invention, FIG. 2 is an enlarged view of FIG. 1, FIG. 3 is an enlarged view showing a state of the stent of the present invention after expansion, and FIG. 4 is a conceptual view of struts constituting a cell.

As shown in FIG. 1, a stent 1 can form a generally tubular body of a plurality of ring units 4 formed of a plurality of cells 6 each and can expand in the radius directions from an inside of the tubular body. The above plurality of cells 6 are connected to one another above and below, and a plurality of such cells 6 are arranged so as to surround a central axis C1 of the stent 1 forming the above tubular body, whereby one ring unit 4 is constituted. A plurality of such ring units 4 are arranged in the axial direction of the stent 1 forming the above tubular body, and adjacent ring units 4 are connected to each other with a connector portion 5 at least in one portion each.

(Cell)

In the present invention, the above cell 6 means one component unit having a configuration consisting of a curved portion and two generally linear struts, and more specifically, as shown in FIG. 2, said curved portion is a >-shaped curved portion 12 and said two generally linear struts are adjacent and continued to said >-shaped curved portion.

In one embodiment, as is shown in FIG. 2, the cell 6 is consisting of >-shaped curved portion 12, having an acute angle X, to which are connected two generally linear struts, one strut containing generally linear portion 11, the other strut containing a curved line portion 13. In FIG. 2, rectangular or box L depicts a space which defines each unit of a cell consisting of the curved portion and two generally linear struts. Of the two struts, at least one strut is disposed in the axial direction (axially-disposed-strut (ADS).

Figure 5:
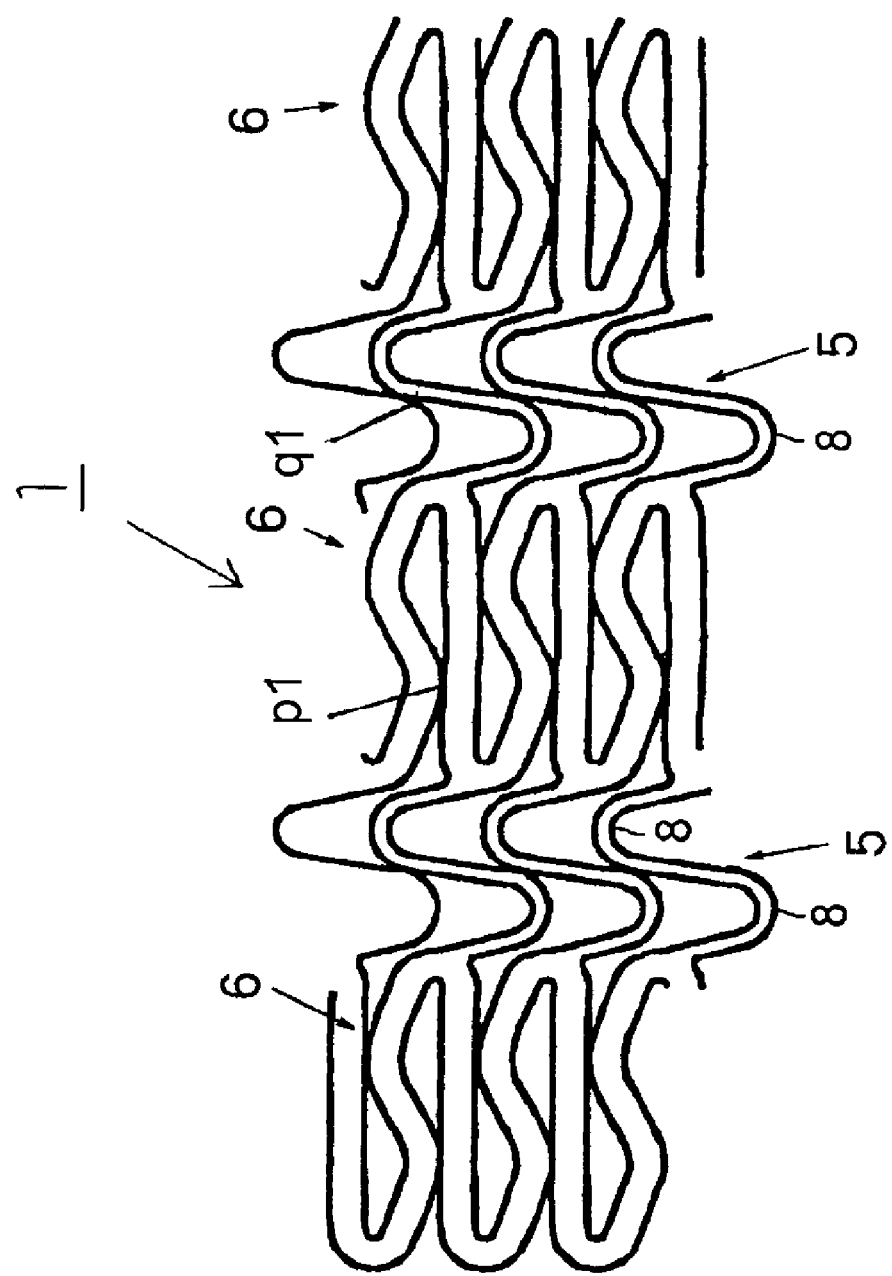
FIG. 5 is an enlarged view of a stent that is decreased in size during delivery to a blood vessel.

The cell is expanded by expanding the >-shaped curved portion as a pivot as shown in FIG. 3, and compressed by bending the >-shaped curved portion as shown in FIG. 5, thus the curved portion 12 in cell 6 is a bendable and expandable (B/E) curved portion.

Further, as shown in FIGS. 2, 4, 7, and 9 when each of the above cell 6 is divided into upper and lower portions with a center line C2 in the axis direction of the stent, the upper and lower portions of the cell are formed asymmetrically with regard to the center line C2, and are formed such that, when the above tubular body, that is, the stent is expanded so that the diameter φ of the stent is, for example 2.5 mm, the curved portion 12 of the cell after expansion comes to have an angle θ of 30° or greater as shown in FIG. 3.

The angle θ of the curved portion 12 after expansion refers to an angle formed between the generally linear portion 11 from a point 0 on the curved portion 12 and that generally linear portion 15 of the curved-line portion 13 which is close to the point 0 side, as shown in FIG. 3.

As shown in FIG. 2, preferably, each cell is constituted of the generally liner portion 11 and the curved-line portion 13 that are connected to each other through the curved portion 12, and the curved line portion 13 has two or more minor curved portions 14 having an obtuse angle Y each.

(Angle of Curved Portion after Cell Expansion)

Figure 6:
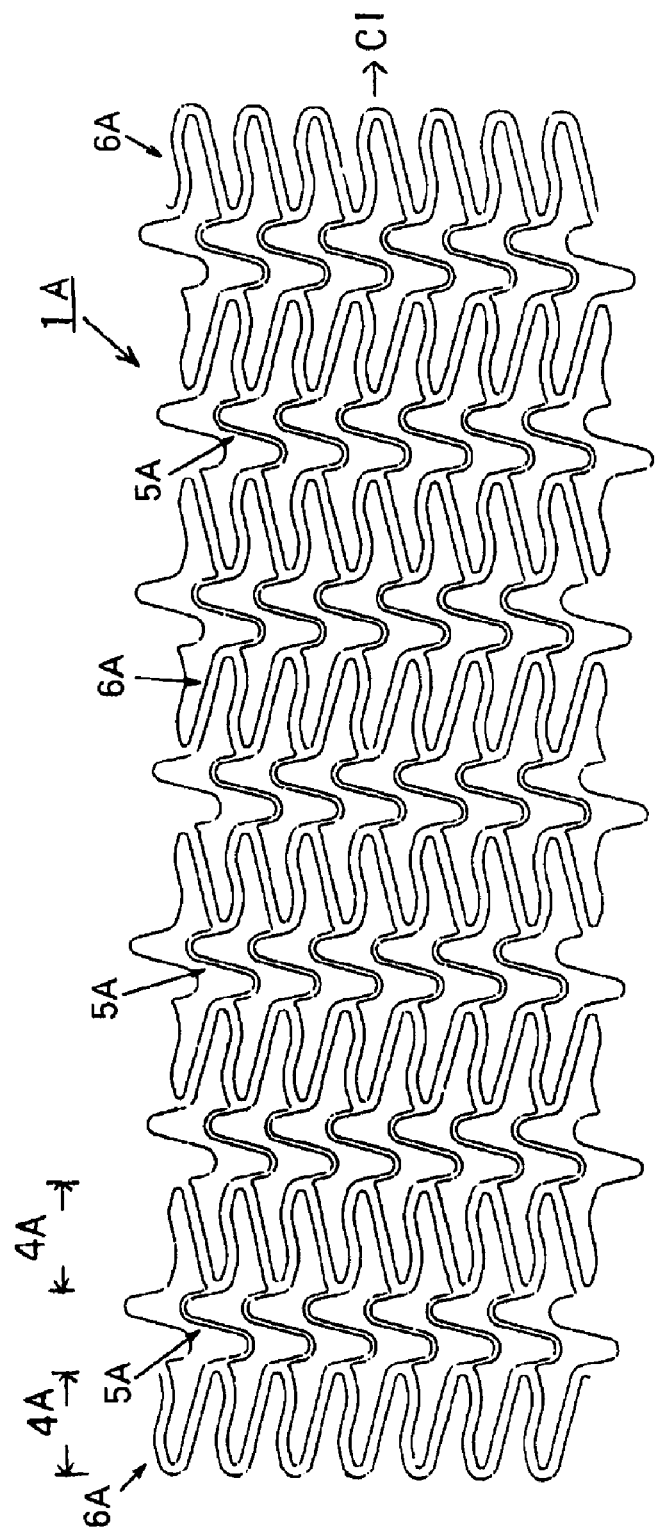
FIG. 6 is a plan view of other embodiment of the stent of the present invention.
Figure 8:
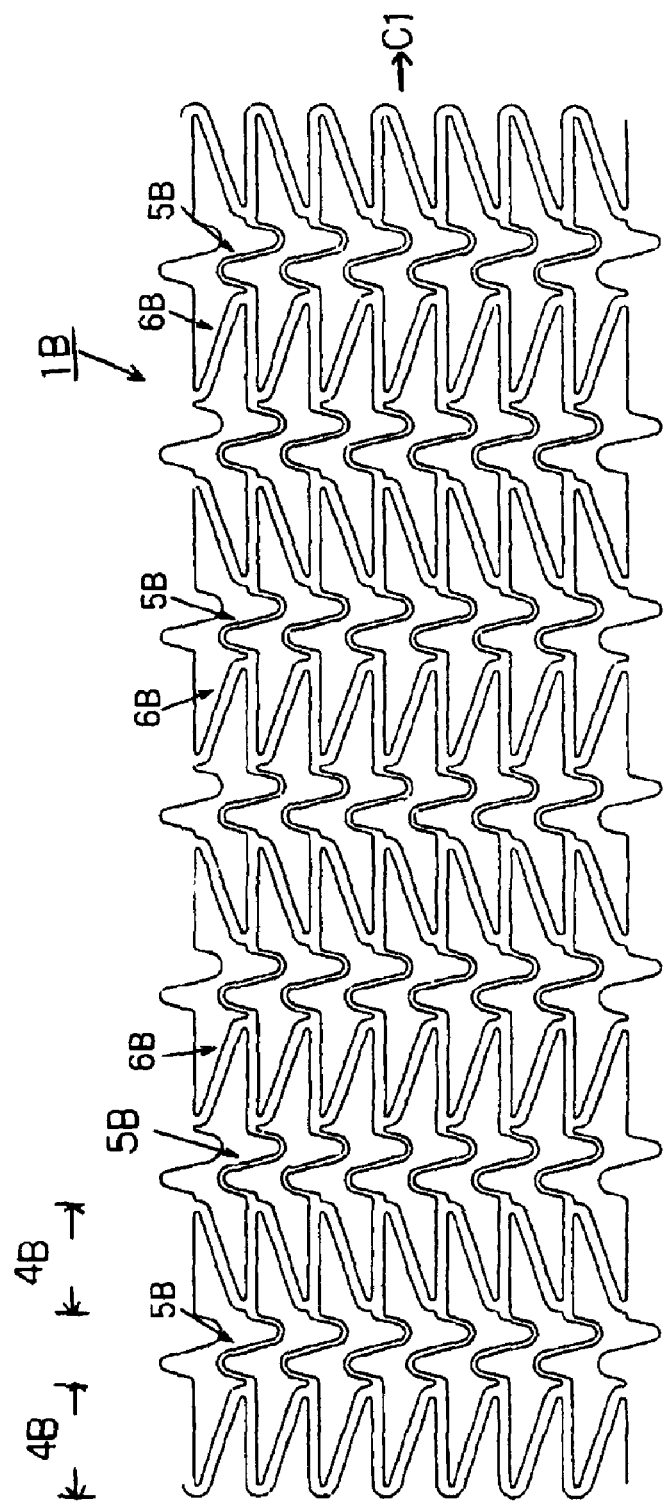
FIG. 8 is a plan view of other embodiment of the stent of the present invention.

The radial sustaining force (to be also referred to as "radial force") of the stent increases, as the generally liner portion 11, the curved portion 12 and the curved line portion 13 (to be also referred to as "generally S-shaped portion" hereinafter) having the minor curved portions 14, which form the cell 6, come to be closer to the perpendicular direction to the central axis C1 of the stent (or tubular body), as shown in FIGS. 1, 6, and 8. That is, as the angle θ of the curved portion 12 after expansion comes closer to 180° as shown in FIG. 3, the radial sustaining force increases. Preferably, therefore, the stent is formed such that when the above tubular body is expanded until it has a diameter φ of 2.5 mm, preferably, 3.0 mm, the angle θ of the above curved portion after expansion is at least 30°.

The above radial sustaining force (radial force) refers to the rigidity of the stent in the circumferential direction (radius direction) of the stent and refers to the degree of easiness with which the stent is deformed in the circumferential direction (radius direction) of the stent. A stent having a high radial force refers to a stent that is not easily deformed in the circumferential direction (radius direction) of the stent when it is inserted and placed deep in a blood vessel of an organism to be exerted an external pressure (outside pressure) from and through a blood vessel wall. That is, in view of the object of the stent, it is essential to create such a stent that can maintain its radial force at a high level.

(Number of Cells Arranged in the Radius Direction)

Further, since the above point has regard to the number of the cells 6 arranged, the number of the cells 6 arranged in the radius direction is preferably 4 or more. Further, when the tubular body, that is, the stent, after expansion has a diameter φ of 3.0 mm or greater, the number of the cells arranged is at least 6, preferably 6 to 12.

(Number of Cells in the Axial Direction and Angle of Curved Portion After Expansion)

The cells are desirably so disposed in number at least 3, preferably 4 to 8, per 10 mm in the axial direction of the stent, in order that the angle θ of the curved portion 12 after expansion is at least 30°, preferably 45° to 140°, more preferably 45° to 120°, when the stent after expansion has an intended diameter (a specification diameter, e.g., φ: 3.0 mm, φ: 4.0 mm).

To arrange the angle θ after expansion in an intended diameter to be closer to 180°, for example, to be more than 140°, is effective for obtaining the sufficient radial sustaining force, which, however, undesirably makes the deformation of the curved portion 12 too large, thereby posing a problem with strength in stent and decreasing the total length of the stent due to expansion (to be referred to as "foreshortening" hereinafter), which causes a problem that exact positioning of the stent to the intended place becomes difficult when the placement of the stent is to be made.

(Thickness, Width, etc., of Cell)

In the present invention, generally, the cell preferably has the following thickness and width. That is, when the angle θ of the curved portion 12 of the above cell is defined as described above, the thickness of the above cell 6 (more precisely the thickness of a strut constituting the cell) is preferably 0.12 mm or less for preventing the thrombus formation. Similarly the thickness of the above cell 6A (the thickness of a strut constituting the cell) is preferably 0.12 mm or less for preventing the thrombus formation. 6A indicates a cell of a stent 1A in FIGS. 6 and 7. Similarly the thickness of the above cell 6B (the thickness of a strut constituting the cell) is preferably 0.12 mm of less for preventing the thrombus formation. 6B indicates a cell of a stent 1B in FIGS. 8 and 9. These reference numerals 6, 6A, and 6B will be used in this sense hereinafter. However, when the cell thickness (thickness of a strut) is too small or less than 0.06 mm, X-ray imaging capability (contrast image formability) and the radial sustaining force decrease, so that the cell thickness (thickness of a strut) is in the range of 0.06 to 0.12 mm, preferably 0.07 to 0.12 mm.

Similarly, with the increase in the width of the cell 6 (6A, 6B), the higher radial sustaining force is more preferably obtained. However, when the width of the cell is too large, the metal area increases and risks of thrombus formation and restenosis increase. On the other hand, when the cell width is too small, no sufficient radial sustaining force can be obtained. Therefore, by taking into account of these, desirably, the cell width in the stent of the present invention is in the range of 0.08 mm to 0.15 mm, preferably 0.08 mm to 0.12 mm.

In the present invention, the thickness and width of the cell 6 (6A, 6B) are defined as described above, and further, the ratio of the length 6L of the cell 6 (6A, 6B) in the axial direction of the stent and the length 5L of the connector portion 5 in the axial direction of the stent is determined to be in a specific range defined in the present invention as will be described later, whereby good X-ray imaging capability, the high radial sustaining force and the high flexibility can all be accomplished and maintained at the same time.

The strut form of the cell is preferably shaped so as to be asymmetric with regard to the center line C2 as shown in FIG. 4(b) rather than is formed so as to be symmetric as shown in FIG. 4(a). That is because of the following. When it is formed asymmetrically, the relative length of the entire strut is larger (for example, a comparison of FIG. 4(a) and FIG. 4(b) inevitably shows $2a<c+d$)), the expandability of the stent itself can be enhanced, and the more effective prevention of the foreshortening can be achieved.

(Connector Portion)

In the stent of the present invention, the connector portion for cell-cell connection is constituted as follows.

For example, the above connector portion 5 connecting the cells 6 and 6 in the stent 1 has at least 2 curved portions as shown in FIG. 2, and has a central generally linear portion 7, to both ends of which are connected curved portions 8 and 8. End portions of the above curved portion 8 are connected to the above cells 6 and 6 constituting different (adjacent) ring units 4 and 4 through connection portions 9 and 9.

The above connector portion 5 is asymmetrically connected to ends of the above cells 6 and 6 as shown in FIG. 2.

(Connector Portion Length, etc.)

Concerning the total length (5L') of the connector portion 5, which is the total length of the generally liner portion 7 and the arched portions 8 and 8, measured along the line, is preferably at least 1 mm, since it is considered that the larger the length of the connector portion, the more improved the flexibility. However, when the above total length is too large, the S-shaped connector portion 5 itself becomes large in size, vertically adjacent connector portions 5 interfere with each other when the stent is mounted on a balloon catheter (the stent on a balloon catheter is sometimes decreased in diameter to some extent) or when the stent is made curved along a blood vessel while it passes through a curved portion of the blood vessel, which interference of connector portions causes impairment of the flexibility. Desirably, therefore, the total length (5L') of the entire connector portion is at least 1 mm, preferably 1 mm to 2 mm. The total length (5L') of the entire connector portion is as described above the length measured along the line of the connector portion.

Further, for the above reasons, desirably, the R (radius) of an arc constituting the curved portion 8 is 0.05 mm or more, preferably 0.05 mm to 0.2 mm.

(Thickness and Width of Connector Portion)

Generally, the thickness and width of the connector portion are preferably defined as follows.

Desirably, the thickness of the above connector portion 5 is as small as 0.12 mm or less for preventing the thrombus formation as described above. Similarly, the thickness of the above connection portion 5A is as small as 0.12 mm or less for preventing the thrombus formation as described above. 5A indicates the connector portion of a stent 1A in FIGS. 6 and 7. Similarly, the thickness of the above connector portion 5B is as small as 0.12 mm of less for preventing the thrombus formation as described above. 5B indicates the connector portion of a stent 1B in FIGS. 8 and 9. These reference numerals 5, 5A, and 5B will be used in this sense hereinafter. However, when the above thickness is too small or less than 0.06 mm, the X-ray imaging capability and the radial sustaining force come to decrease, so that the thickness of the connector portion is in the range of 0.06 to 0.12 mm, preferably 0.07 to 0.12 mm.

When the width of the connector portion 5 (5A, 5B) is too large, the flexibility decreases. When it is too small, it involves risk of breaking when the stent is curved. Desirably, therefore, the above width is 0.1 mm or less, more preferably in the range of 0.04 to 0.10 mm, still more preferably 0.04 to 0.08 mm.

For improving the flexibility, the width of the connector portion 5 (5A, 5B) is preferably smaller than that of the cell 6 (6A, 6B).

(Ratio of Length of Cell and Length of Connector Portion)

In this invention, concerning the ratio of the length 6L of the above cell 6 in the axial direction of the stent and the length 5L of the above connector portion 5 in the axial direction of the stent as shown, for example, in FIG. 2, on the basis that when the length 6L is taken as 100, the length 5L is 50 to 100, preferably 55 to 80, more preferably 57 to 70, most preferably 58 to 65.

Further, concerning the ratio of the length 6L of the above cell 6 in the axial direction of the stent and the total length 5L' of the generally linear portion 7 and the curved portions 8, on the basis that when the length 6L is taken as 100, desirably, the length 5L' is 50 to 150, preferably 100 to 150.

It has been found that by defining the ratio of the length of the stent and the length of the connector portion as described above, the flare phenomenon after expansion of the stent or during delivery of the stent can be suppressed, and further, the radial sustaining force can be maintained at a high level and the stent itself can be provided with flexibility.

(Pattern of Stent)

The pattern of the stent of the present invention as the following features.

As shown in FIG. 2, for example, in the stent 1, the cells 6 are asymmetrically arranged through the connector portions 5 with regard to the center line C2 in the axial direction of the stent, while the cells 6 are arranged in the same direction and at the same height in the axial direction of the stent. That is, the cells 6 positioned in the axial direction of the stent are arranged such that when the cells in an n-th column are moved to an (n+1)-th column in the axial direction of the stent, the cells in the n-th column lie overlapped on the cells in the (n+1)-th column. Further, the cells 6 are arranged in the same radius direction such that when the cells 6 in the same column (of the same ring unit) are shifted upward or downward, one cell overlaps on another cell. While the generally linear portion 11 of each cell is basically nearly horizontal (nearly in parallel) with regard to the center line C2, the generally linear portion 11 may tilt to some extent with an angle so long as the angle θ of the curved portion 12 after expansion does not come to be less than 30°.

(Pattern of Connector Portion)

As far as the pattern of the connector portions is concerned, each of the connector portions 5 is also arranged through the cell 6 asymmetrically in the axial direction of the stent, and the connector portions 5 are arranged in the same direction with regard to the axial direction of the stent and at the same height. That is, the connector portions 5 positioned in the axial direction of the stent are arranged such that when the connector portions in an n-th column are moved to an (n+1)-th column in the axial direction of the stent, the connector portions in the n-th column lie over lapped on those in the (n+1)-th column. Further, the connector portions 5 are arranged in the same radius direction of the stent such that when the connector portions in the same column (of the same ring unit) are shifted upward or downward, one connector portion overlaps on another connector portion.

Preferably, the cells 6 and the connector portions 5 in the axial direction of the stent are arranged such that the height of the cells 6 is not the same as, and differs from, the height of the connector portions 5. As already discussed, in the stent of the present invention, preferably, the width of the strut constituting the cell is greater than that of the strut constituting the connector portion 5.

In the stent 1 of the present invention, those factors such as the angle θ of the curved portion 12 of the cell after expansion, the ratio of the length 6L of cell 6 in the axial direction of the stent and the length 5L of the connector portion 5 in the axial direction of the stent, the forms of the above mentioned connector portion and the cell and the layouts (pattern) of the connector portions 5 and the cells 6 in the radius and axial directions of the stent, are defined as described above. By defining these factors as were described, there is caused no overlapping of the cells 6 and the connector portions 5 each other in the radius direction of the stent, when the diameter of the stent 1 is decreased during delivery into a blood vessel as shown in FIG. 5. That is, the stent 1 is formed such that when the diameter of the stent 1 is decreased as shown in FIG. 5 causing strut-strut contact p1 and connector-connector contact q1, the cell 6 and the connector portion 5 can be accommodated into a space S present between the cell 6 and the connector portion 5 in the radius direction of the stent as shown in FIG. 2.

Other Embodiments of the Stent

Figure 7:
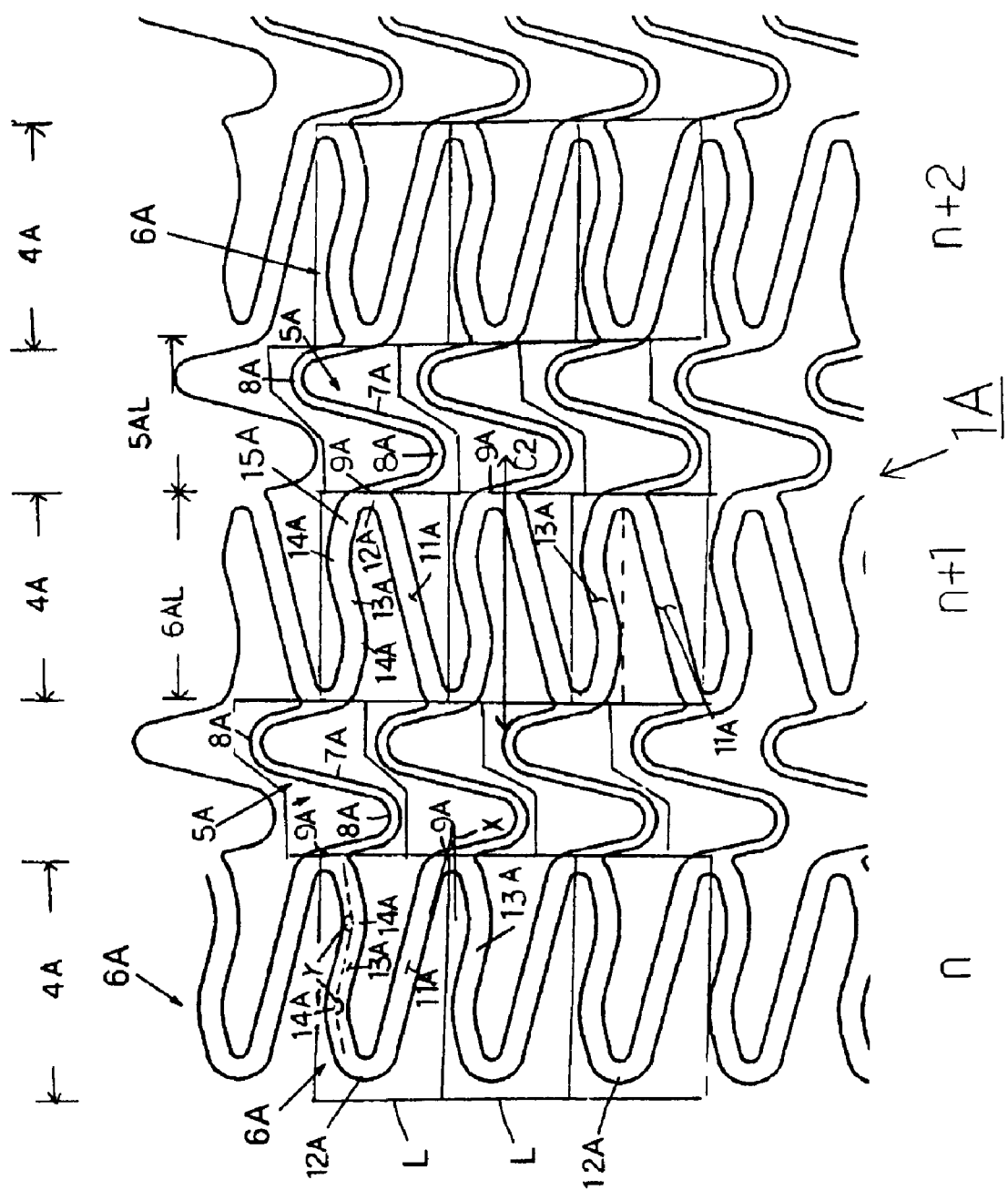
FIG. 7 is a partial enlarged plan view of FIG. 6.
Figure 9:
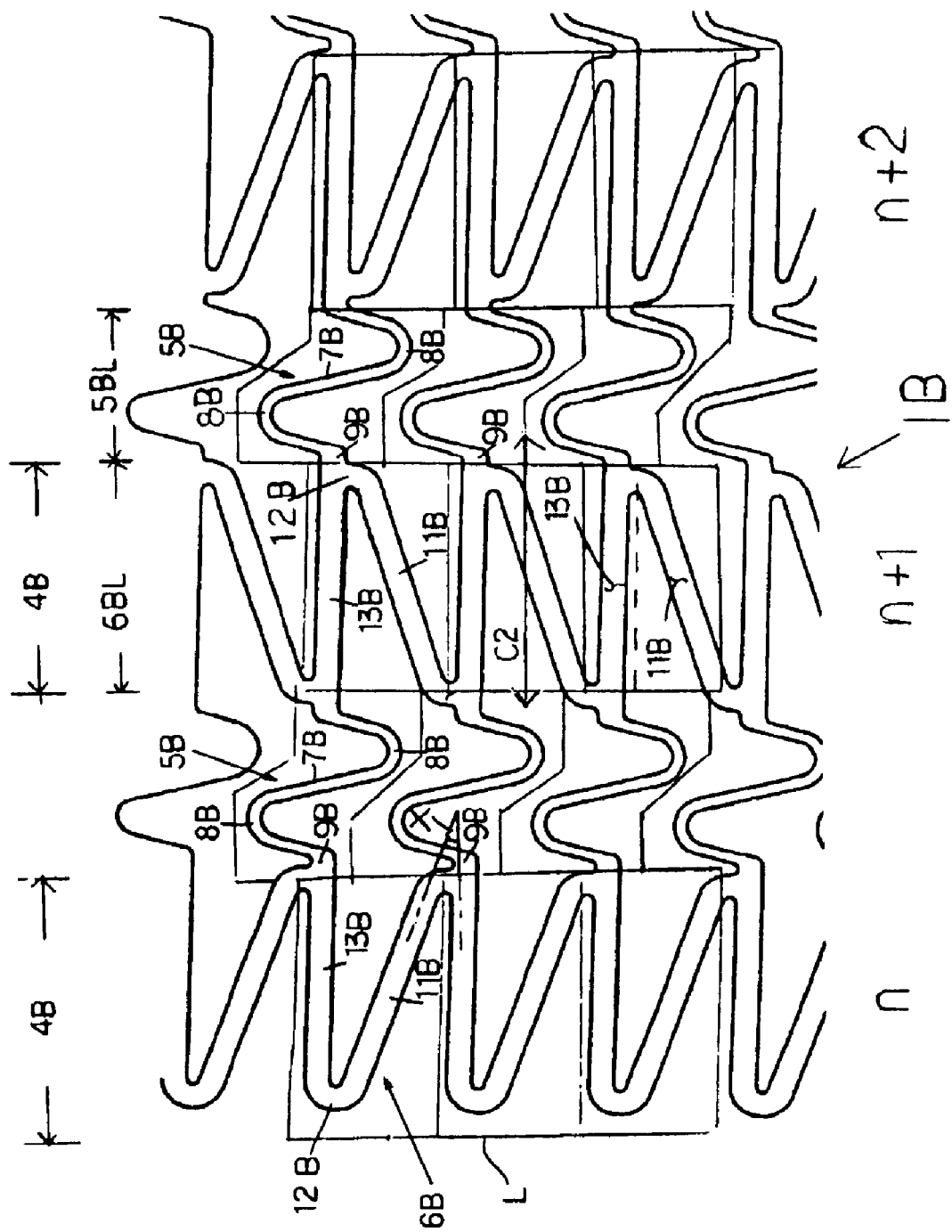
FIG. 9 is a partial enlarged plan view of FIG. 8.

FIGS. 6 and 8 are plan views of other embodiments of the stent of the present invention. FIGS. 7 and 9 are respectively partial enlarged plan view of FIGS. 6 and 8.

(Stent 1A)

The stent 1A shown in FIGS. 6 and 7 is basically the same as the stent 1 shown in FIG. 1 except for the following points. That is, the stent 1A differs in the following points.

(a) Each cell 6A is constituted of a generally linear portion 11A having an acute angle X with respect to the center line C2 in the axial direction of the stent 1A and a curved line portion 13A, the generally linear portion 11A being connected to the curved line portion 13A through a curved portion 12A (in contrast, each cell 6 of the stent 1 is constituted of the generally linear portion 11 arranged nearly horizontally to (nearly in parallel with) the center line C2 in the axial direction of the stent 1 and the curved line portion 13, with the generally linear portion 11 being connected to the curved line portion 13 through the curved portion 12.).

(b) The cells 6A are arranged in the axial direction of the stent 1A symmetrically with regard to the connector portions 5A.

(c) The cells 6A positioned in the axial direction of the stent 1A are arranged such that when the cells in every two columns are taken or viewed in the axial direction of the stent 1A, the cells in an n-th column lie overlapped on the cells in the (n+2)-th column. The other members and definitions of these members are the same as those in the stent 1, so that a detailed explanation thereof is omitted.

(Stent 1B)

The stent 1B shown in FIGS. 8 and 9 differs from the stents 1 and 1A shown in FIGS. 1, 6 and 7 in the following points. That is, the stent 1B basically differs in the following points.

(a) The stent 1B differs from the stents 1 and 1A in that each cell 6B is constituted of a generally linear portion 11B having an acute angle X with respect to the center line C2 in the axial direction of the stent 1B and a generally linear portion 13B arranged nearly horizontally to (nearly in parallel with) the center line C2 in the axial direction of the stent 1B, with the generally linear portion 11B and the generally linear portion 13B being connected through a curved portion 12B. (In contrast, in the stent 1 or 1A, the cell 6 or 6A is constituted of the generally linear portion 11 or 11A and the curved line portion or 13A connected through the curved portion 12.)

(b) The cells 6B are arranged symmetrically in the axial direction of the stent 1B with regard to the connector portion 5B.

(c) The stent 1B differs from the stent 1 but is substantially the same as the stent 1A in that the cells 6B positioned in the axial direction of the stent 1B are arranged such that when the cells in every two columns are taken or viewed in the axial direction of the stent 1B, the cells in an n-th column lie overlapped on the cells in the (n+2)-th column. The other members and definitions of these members are the same as those in the stents 1 and 1A, so that a detailed explanation thereof is omitted.

(Layout of Connector Portions)

In the above stent 1, 1A or 1B of the present invention shown in FIG. 1, 6 or 8, the connector portions 5, 5A or 5B of the cells 6, 6A or 6B constituting each ring unit 4, 4A or 4B are continuously arranged without any omission or skipping in the radius direction of the stent 1, 1A or 1B. However, the connector portions may be arranged by omitting or skipping every other one connector portion or omitting or skipping every other one or two connector portions to form spaces, thereby allowing the entire stent 1, 1A or 1B to become more flexible and it is expected that the more improved delivery of the stent to a branched blood vessel is made.

(Materials, etc.)

The material for constituting the stent 1, 1A or 1B of the present invention can be selected from known materials, and no special limitation is imposed thereon. The stent 1, 1A or 1B is formed, for example, from a pipe made of stainless steel such as SUS316L, a shape-memory alloy such as a Ti—Ni alloy or a Cu—Al—Mn alloy, a Cu—Zn alloy, an Ni—Al alloy, titanium, a titanium alloy, tantalum, a tantalum alloy, platinum, a platinum alloy, tungsten or a tungsten alloy, for example, by a laser processing method.

Further, the stent formed of the above metal may be surface-coated with a biocompatible polymer material such as polyurethane, polyvinyl pyrrolidone or polyvinyl alcohol or the like, with a material formed by immobilizing a physiologically active substance such as heparin or urokinase or the like to the above polymer material by chemical bonding, or with a mixture of the above polymer material and an antithrombotic drug such as argatroban, cilostazol or sarpogrelate hydrochloride or the like.

EXAMPLE 1

Figure 10:
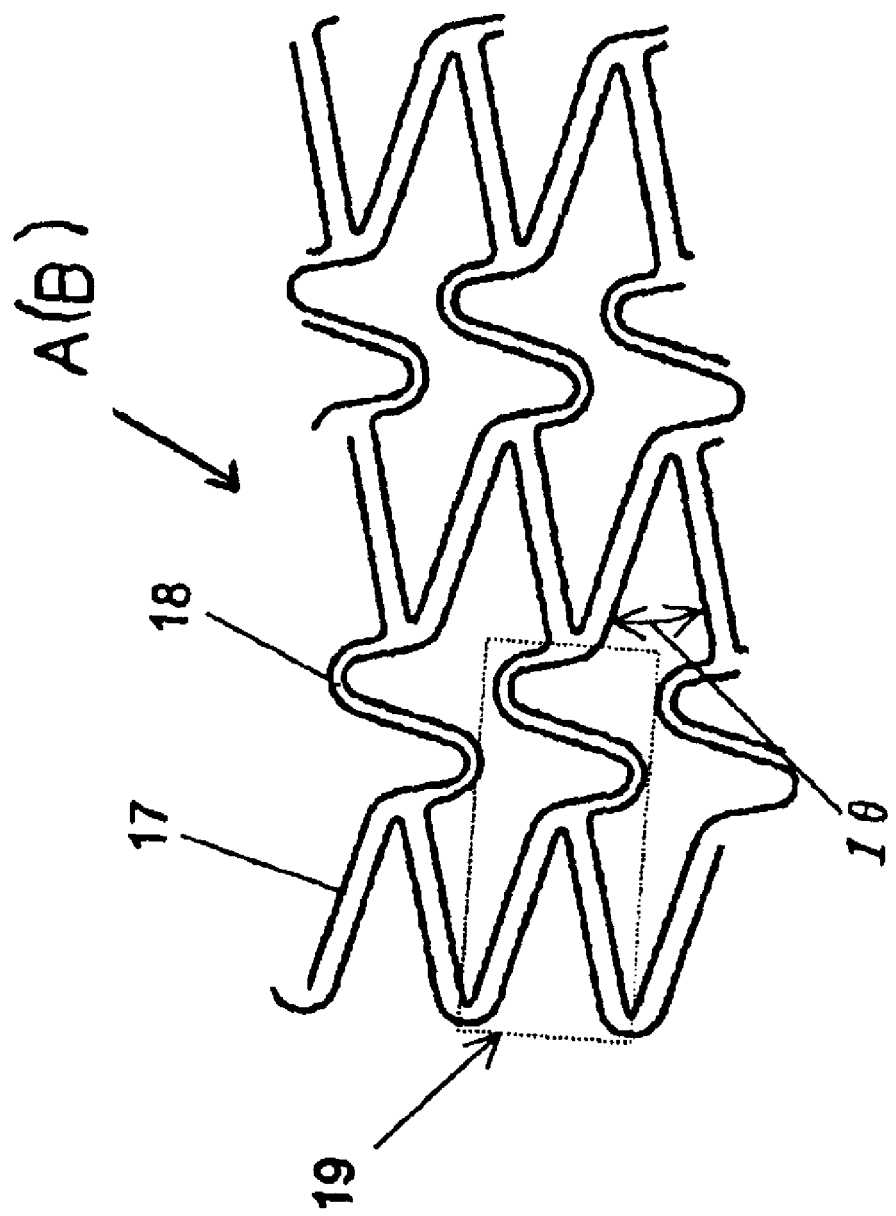
FIG. 10 is an enlarged view of a reference example of the stent of the present invention.

For evaluating a difference in radial sustaining force depending upon an angle after expansion in a stent A(B) constituted of components 19 formed of a generally-<-shaped cell 17 and a generally-S-shaped connector portion 18 each as shown in FIG. 10, there were prepared two stents, each stent having the components 19 different in number in the circumferential direction, a stent A (number of arranged components: 8) and a stent B (number of arranged components: 6) and the stents were evaluated for radial sustaining forces and compared.

Stent A:

| | |
|---|---|
| Number of arranged component 19 | 8 |
| Width of strut of cells 17 | 0.12 mm |
| Thickness of strut of cells 17 | 0.10 mm |
| 1 θ angle after expansion to 3 mm | 60° |

Stent B:

| | |
|---|---|
| Number of arranged component 19 | 6 |
| Width of strut of cells 17 | 0.12 mm |
| Thickness of strut of cells 17 | 0.10 mm |
| 1 θ angle after expansion to 3 mm | 81° |

For the evaluation, each stent was expanded so as to have a diameter φ of 3 mm and placed in a silicon tube placed in a chamber, then, pressure was applied into the chamber, and the stents were measured for changes in outer diameter. Table 1 shows the measurement results.

TABLE 1

| (Results of measurement of radial sustaining force) | | |
|---|---|---|
| | Stent A | Stent B |
| Change in outer diameter during application of pressure at 0.02 MPa | −0.07 mm | −0.04 mm |

As is clear from Table 1, the stent B having a larger angle (1θ) after expansion showed a change of −0.04 mm in outer diameter (the outer diameter decreased by 0.04 mm), and the stent A showed a change of −0.07 mm in outer diameter (the outer diameter decreased by 0.07 mm), so it was confirmed that the stent B had a smaller change in outer diameter and had a greater radial sustaining force.

EXAMPLE 2

Figure 11:
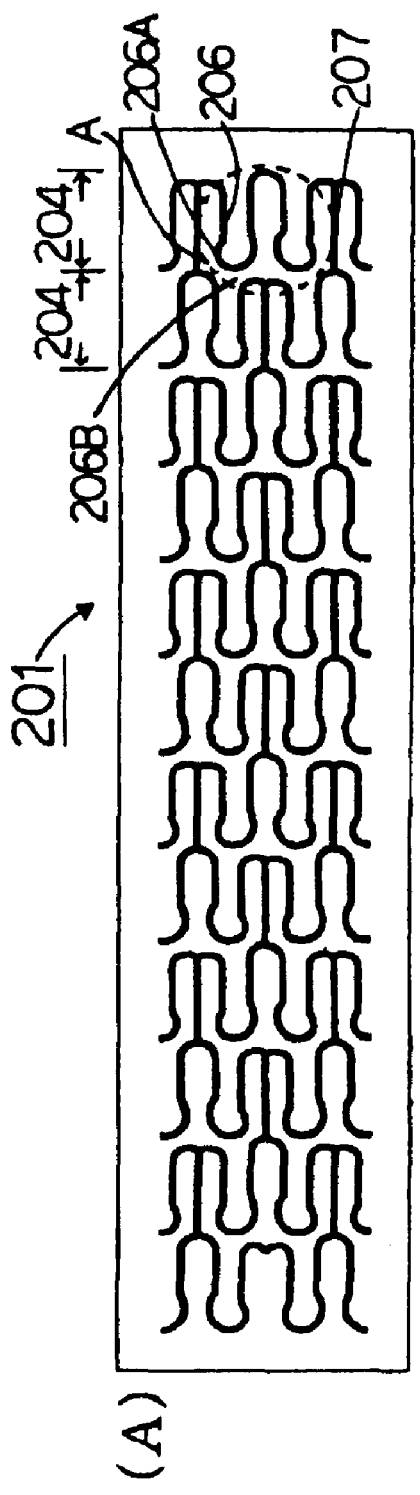
FIGS. 11 and 12 show plan views of conventional stents.
Figure 11:
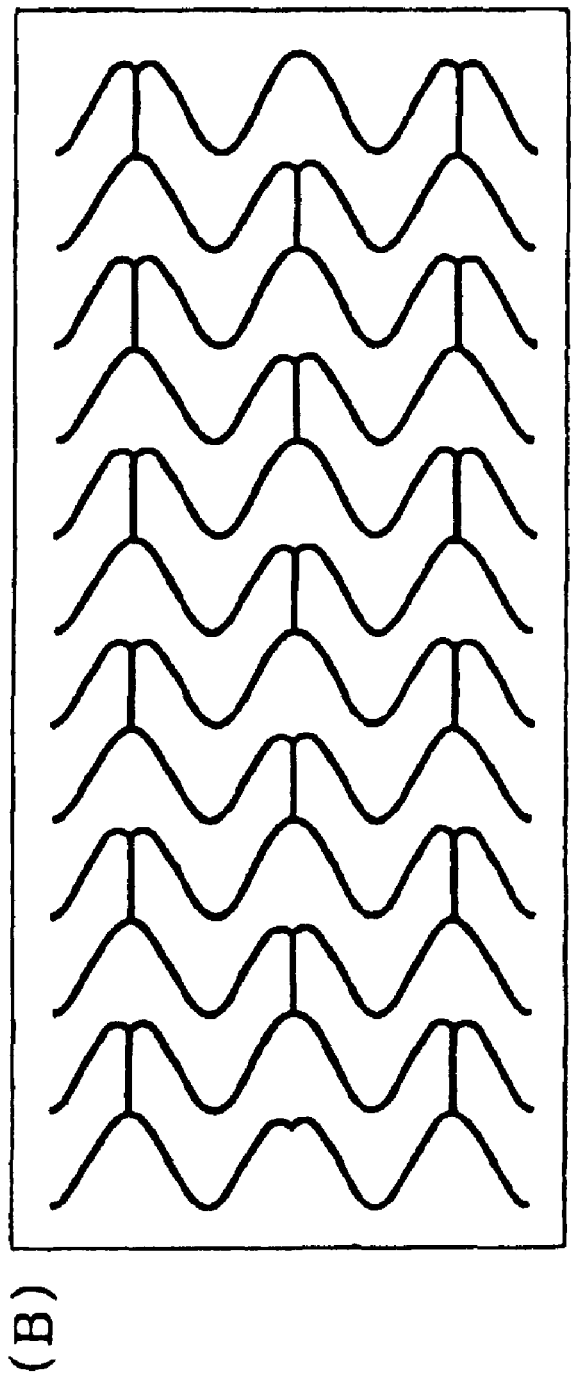
Figure 12:
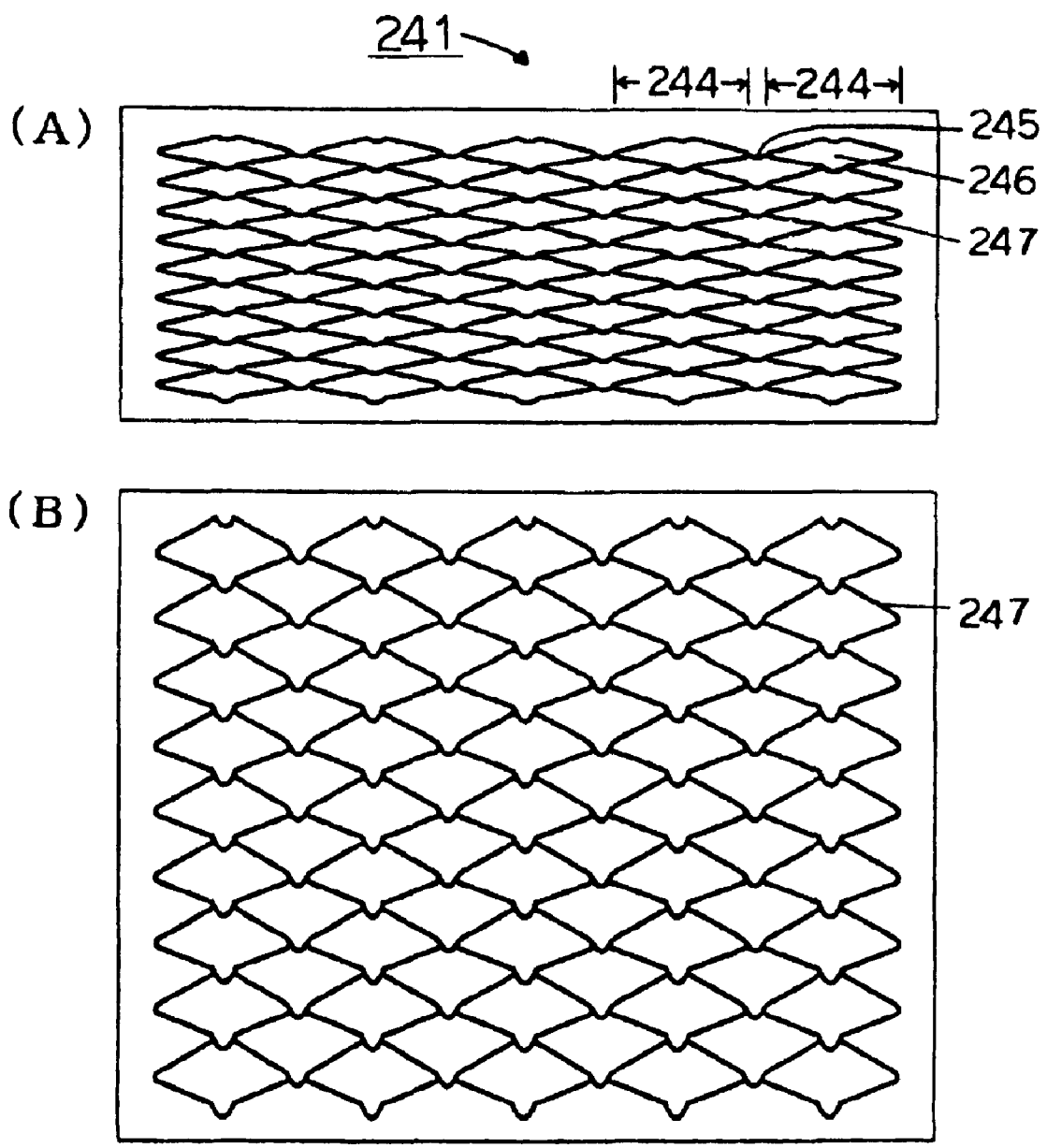

A stent shown in FIG. 1 was prepared, and the radial sustaining force thereof was compared with the counterparts of conventional stents 201 (FIG. 11) and 241 (FIG. 12). Further, the flexibility of the prepared stent was compared with that of the stent 201. In the stent 1, the ratio of the length 6L of the cell 6 in the axial direction of the stent and the length 5L of the connector portion 5 in the axial direction of the stent was determined such that on the basis that the length 6L of the cell 6 in the axial direction of the stent was taken as 100, the length 5L of the connector portion 5 in the axial direction of the stent was made 59. The stent was evaluated for a radial sustaining force in the same manner as in Example 1, and it was evaluated for flexibility by a four-point bending method. Table 2 shows the results of measurement of the radial sustaining force, and Table 3 shows the results of measurement of the flexibility.

TABLE 2

(Results of measurement of radial sustaining force)

|  | Stent 1 | Stent 201 | Stent 241 |
|---|---|---|---|
| Change in outer diameter during application of pressure at 0.02 MPa | −0.026 mm | −0.05 mm | −0.030 mm |

TABLE 3

(Results of measurement of flexibility)

|  | Stent 1 | Stent 201 |
|---|---|---|
| Flexural strength | 11.7 N · mm | 17.1 N · mm |

As is clear from Table 2, it has been confirmed that the stent 1 of the present invention shows a smaller change in outer diameter than any one of the stents 201 and 241, and as is clear from the results in Table 3, it has been confirmed that the stent 1 of the present invention has lower flexural strength than the stent 201. Thus, it has been made clear that the stent 1 of the present invention has both a high radial sustaining force and flexibility as described above.

EXAMPLE 3

A stent 1A shown in FIG. 6 (FIG. 7) and a stent 1B shown in FIG. 8 (FIG. 9) were measured and evaluated for radial sustaining forces and flexibility in the same manner as in Examples 1 and 2. In the stent 1A or the stent 1B, the ratio of the length 6AL, 6BL of the cell 6A, 6B in the axial direction of the stent and the length 5AL, 5BL of the connector portion 5A, 5B in the axial direction of the stent was determined and formed such that on the basis that the length 6AL, 6BL of the cell 6A, 6B in the axial direction of the stent was taken as 100, the length 5AL, 5BL of the connector portion 5A, 5B in the axial direction of the stent was 59. Table 4 shows the results of measurement of the radial sustaining force, and Table 5 shows the results of the flexibility. As is clear from Tables, it has been shown that the stent 1A and the stent 1B give substantially the same results as those of the stent 1.

TABLE 4

(Results of measurement of radial sustaining force)

|  | Stent 1A | Stent 1B | Stent 201 | Stent 241 |
|---|---|---|---|---|
| Change in outer diameter during application of pressure at 0.02 MPa | −0.033 mm | −0.031 mm | −0.05 mm | −0.030 mm |

TABLE 3

(Results of measurement of flexibility)

|  | Stent 1A | Stent 1B | Stent 201 |
|---|---|---|---|
| Flexural strength | 13.7 N · mm | 14.3 N · mm | 17.1 N · mm |

EXAMPLE 4

The stents 1, 1A and 1B of the present invention were measured for foreshortening values when the stents were expanded until they had a diameter φ of 3.0 mm. In the measurement, each stent was measured for a length before the expansion (L1), and each stent was measured for a length after the expansion (L2) up to a diameter φ of 3.0 mm. And, a decrease ratio of the total length was calculated on the basis of the following equation and used as a foreshortening value.

Foreshortening value=$((L1-L2)/L1) \times 100$

For comparison, the stents 201 and 241 were measured in the same manner. Table 6 shows the results.

TABLE 6

|  | Stent 1 | Stent 1A | Stent 1B | Stent 201 | Stent 241 |
|---|---|---|---|---|---|
| Foreshortening value | 1.5% | 1.5% | 3% | 5.6% | 5.6% |

As is clear from Table 6, it has been confirmed that the stents 1, 1A and 1B of the present invention show a very small foreshortening value than the conventional stents 201 and 241.

On the basis of the above fully-described technical knowledge or information, the present inventors have further advanced the conception of the technical feature of the stent of the present invention for more accurately complying with higher demands in the high-tech health care, medical fields such as cardiac surgery, cerebral surgery, and the like.

That is, according to the present invention, there is provided an ultimate stent that is constituted with greatest accuracy and highly sophistication capable of satisfying any properties required as a stent when it is practically used in the above medical fields, as will be described below.

The basic technical conception of the highly-sophisticated stents 1, 1A and 1B of the present invention (objects of the invention) is to create a stent having following properties or characteristics.

First, the already discussed radial supporting force (rigidity in the circumferential direction (radius direction)) is to be maintained at a higher level. That is, even in a case where an external force is exerted on the circumference so as to depress and crush the stent, the stent is not to be easily deformed in the circumferential direction (radius direction).

Second, the bending flexibility (easiness in expanding and contracting of the size in the axial direction of the stent) is to be maintained at a high level. That is, the stent is to have rigidity with which it is not easily deformed in the radius direction and is also to be easily extendable and contractible in the axial direction.

(High Radial Force)

For accomplishing the first object ("to maintain the radial force at a higher level"), basically, (1) the stent is to be set such that the curved portion 12 (12A, 12B) of the cell 6 (6A, 6B) after expansion comes to have a large angle θ (that is, 30° or more, preferably in the range of 45° to 140°).

(2) For bringing the angle θ into the above range, preferably, the smaller is the number of the cells 6 (6A, 6B) arranged in the circumferential direction, the better is the results. When the above number of the cells is too large, undesirably, it is impossible to design the angle θ sufficiently large after expansion. For example, when the stent comes to have a diameter ϕ of 3.0 mm or greater after expansion, desirably, the number of the cells arranged is 6 or more, preferably 6 to 12.

(High Bending Flexibility)

For accomplishing the second object ("to maintain the bending flexibility at a higher level"), first, (3) it is preferable that the number of the cells 6 (6A, 6B) arranged in the axial direction of the stent should be large enough, for example, desirably, the number of the cells is at least 3, preferably 4 to 8, per 10 mm of the length of the stent.

Further, (4) importantly, the length 5L of the connector portion 5 (5A, 5B) in the axial direction of the stent is to be made sufficiently large, as large as is possible, or the total length 5L', the generally linear portion 7 and the curved portion 8 combined, is to be made long enough, as long as is possible. In the above connector portion 5 (5A, 5B), therefore, it is to be preferably configured that the entire length 5L' thereof per unit surface area of the stent should be sufficiently large as possible.

(5) For configuring the entire length 5L' of the connector portions to be as large as possible, the connector portions preferably have a form as will be described below.

(a) The form of the connector portion 5 (5A, 5B) is preferably a generally-S-shaped form when its relationship to the entire length 5L' is taken into account. If the connector portion is made to have a linear constitution, when two or more such linear connector portions are arranged in the circumferential direction to connect the cells, undesirably, the stent itself inevitably loses bending flexibility.

(b) A generally W-shaped form is not preferred since with such shape curved portions are larger in number. When a stent with generally W-shaped connector portions is inserted into a tortuous curved blood vessel, placed in and along the curved blood vessel, in such a state, expanded and then fixed, inwardly curved connector portions of the stent (more precisely, many curved portions) easily come to overlap and interfere with one another.

For avoiding the above interference of the connector portions, for example, it is required to increase the radius (distance) of each curved portion 8 in order to increase the length 5L. When the radius (distance) of the curved portion 8 is increased too much so that 5L is excessively long, undesirably, the ratio of the connector portions 5 to the entire stent surface area (ratio thereof to the cell portions 6) is too large, thereby making it difficult to obtain the sufficient radial sustaining force required.

(c) When the connector portions have a generally-U form, in principle, the length of the member constituting the connector portion relative to the unit surface area of the stent cannot be increased enough, which causes, undesirably, the stent poor in bending flexibility.

As described above, the form of the connector portion is preferably a generally S-shaped one, and for maintaining the flexibility after expansion, preferably, the length 5L, 5L' of the connector portion 5 (5A, 5B) is such that the above generally S-shaped form can be maintained after expansion as shown in FIG. 3.

(Ratio of Length of Cell and Length of Connector Portion)

For providing high bending flexibility to the stent, it is preferred to increase the length 5L, 5L' of the connector portion 5 (5A, 5B) as described above. At the same time, however, it is required to prevent the flare phenomenon after expansion of the stent or during delivery and also maintain the radial force at a high level. It is therefore necessary to configure a suitable length by taking into account the above facts and the relationship between the length 6L, etc., of the cell 6 (6A, 6B) in the axial (longitudinal) direction of the stent and the length 5L, 5L' of the connector portion 5 (5A, 5B).

That is, the ratio of the length 5L (5AL, 5BL) of the above connector portion 5 (5A, 5B) in the axial direction of the stent and the length 6L (6AL, 6BL) of the cell 6 (6A, 6B) in the axial direction of the stent is configured such that when 6L (6AL, 6BL) is taken as 100, the 5L (5AL, 5BL) based thereon is 50 to 100, preferably 55 to 80, still more preferably 57 to 70, most preferably 58 to 65. Under the above conditions, importantly, the length 5L, 5L' of the connector portion 5 (5A, 5B) is configured as large as possible, and the generally liner portions 7 and the curved portions 8 of the connector portions 8 are so arranged that they do not mutually interfere while the stent is being flexed or bent.

Further, as already discussed, the ratio of the length 6L (6AL, 6BL) of the above cell 6 (6A, 6B) in the axial direction of the stent and the total length 5L', for example, of the generally liner portion 7 and the curved portions 8 of the connector portion 5 (5A, 5B) is preferably formed such that when 6L or the like is taken as 100, 5L' based thereon is 50 to 150, preferably 100 to 150.

With the above features considered, the flare phenomenon after expansion of the stent or during delivery can be prevented, the radial sustaining force is able to be maintained at a high level and the stent per se can also be provided with flexibility, as are described already.

(Flexibility of Connector Portion at the Outermost Ends of the Stent)

Further, in the present invention, preferably, the connector portions 5 (5A, 5B) at the outermost ends (both ends) of the stent are formed to be softer as compared with the connector portions on the inward side of the stent. In this manner, the stent is provided with flexibility during insertion thereof into a blood vessel and can be easily inserted into a blood vessel. For forming the connector portions at the outermost ends of the stent to be softer as compared with the connector portions on the inward side of the stent, the length 5L, 5L' at each end is to be made larger than that on the inward side, or the width thereof is to be made smaller than that on the inward side.

For example, in FIG. 1 (FIG. 2), FIG. 6 (FIG. 7) or FIG. 8 (FIG. 9), in order to provide the end portions of the stent with more flexibility, it is configured that connector portions 5 (5A, 5B) on the first column on the left and the connector portions 5 (5A, 5B) on the first column on the right are to be formed so as to have a larger length 5L, 5L', or so as to have a smaller width, than the connector portions 5 (5A, 5B) arranged in columns between them.

Specifically, on the basis that the length 5L, 5L' and width of the connector portion 5 (5A, 5B) inward side of the stent are both taken as 100, the length 5L, 5L' of the connector portion 5 (5A, 5B) on each end of the stent is in the range of 120 to 200, preferably 140 to 180, and the width thereof is in the range of 95 to 50, preferably 80 to 60, thereby the end portions of the stent are provided with preferable flexibility.

(Form of Cells)

The cell 6 (6A, 6B) preferably has such a form that the stent can be easily mounted on a balloon catheter, in other words, such that struts on the entire stent surface do not interfere with one another when the stent is decreased in diameter and such that capable of maintaining the easily-expandable shape when expansion is made.

For this purpose, as forms of cell, for example, there is preferably employed a form or configuration in which at least one generally linear portion 11 (11A) and the curved line portion (13A) are connected through the curved portion 12 (12A) as shown in FIG. 2 or FIG. 7, or a form in which the generally linear portion 11B having an acute angle X with respect to the center line C2 in the axial direction of the stent 1B is connected to the generally linear portion 13B arranged nearly horizontally to the center line C2 in the axial direction of the stent 1 through the curved portion 12B as shown in FIG. 9.

When the above described cell configurations are employed, the cell 6 can further have a longer strut as compared with a case where a liner-strut-conformation is made, so that the generally linear portion 11 (11A) and the curved line portion (13A) constituting the cell 6 in the stent 1 (1A) can be made substantially equal to each other. In this manner, the area of the defined cell portion 6 can be effectively utilized, and the above cell form is also effective for preventing a decrease in length in the longitudinal direction (foreshortening) during expansion.

As already described, the struts of the cell 6 are preferably formed asymmetrically with respect to the center line C2 in the axial direction of the stent as shown in FIG. 4(b), and thereby, the relative length of the entire struts is made larger, the stent itself is provided with high expansion capability, and the more effective prevention of the foreshortening can be accomplished with this stent.

INDUSTRIAL UTILITY

Basically, the stent of the present invention fully secures both high flexibility and high radial sustaining force (radial force (rigidity in the circumferential direction)), and further, preferably, it secures both high radial force and high bending flexibility (easiness in increasing and decreasing a size in the axial direction of the stent (expansion and contraction)), which causes an improvement in the vascular-dilation capability and the effective prevention of foreshortening and flare phenomenon are made. The stent of the present invention thus can be used very suitably as a stent for securing a necessary intravascular or luminal region by dilating a stenosed portion, etc., of a blood vessel and the like.

The invention claimed is:

1. A stent with high bending flexibility, which has a generally tubular body formed of a plurality of ring units, and said tubular body is expandable in the radial direction of said tubular body from inside of said tubular body,
   each of the plurality of ring units being formed of a plurality of cells connected to one another circumferentially around a central axis (C1) of the stent forming said tubular body,
   said ring units being arranged in an axial direction along the central axis (C1) of the stent forming said tubular body such that adjacent ring units are connected to each other with connector portions,
   (i) each of said connector portions being generally S-shaped and formed of two arched portions, each arched portion having an arch of curvature radius R, and a generally linear portion therebetween, wherein each connector portion is connected to at least one cell of one of the plurality of ring units and at least one cell of an adjacent ring unit,
   (ii) wherein each of said cells has a first configuration comprising a bendable and expandable curved portion having acute angle X, a first strut comprising a generally linear portion having an axially disposed position that is substantially parallel to the central axis (C1) of the tubular bodied stent, and a second strut comprising at least one curved line portion and at least one generally linear portion,
   wherein the generally linear portion of the first strut is adjacent and continued with the bendable and expandable curved portion and the generally linear portion of the second strut is adjacent to and continued with the bendable and expandable curved portion,
   wherein a longitudinal axis of the first strut and a longitudinal axis of the generally linear portion of the second strut intersect to form the acute angle X of said bendable and expandable curved portion,
   (iii) wherein in the first configuration, the cells and the connector portions are so disposed such that there is at least one of a first space between each first strut and each adjacent second strut (Si), a second space between each bendable and expandable curved portion and each adjacent arched portion of each connector portion (Sii), and a third space between adjacent arched portions of adjacent connector portions (Siii),
   (iv) wherein when compression of the stent in the radial direction is made, each of said cells has a compressed configuration, wherein the first strut maintains the axially disposed position and the second strut bends toward said first strut,
   wherein in the compressed configuration at least part of adjacent first and second struts make contact and at least part of adjacent connector portions make contact,
   wherein said cells are arranged in the axial direction of the stent such that 3 to 8 cells are disposed per 10 mm of the length of said stent,
   wherein the ratio of the length of each cell in the axial direction of the stent and the length of each connector portion in the axial direction of the stent is 50 to 100, and
   wherein said stent with said cells in said compressed configuration is configured to be mounted on a balloon and transported in a blood vessel to a diseased part to be treated.

2. The stent as recited in claim 1, wherein said cells have a thickness of 0.06 mm to 0.12 mm and a width of 0.08 mm to 0.15 mm and said connector portions have a thickness of 0.06 to 0.12 mm and a width of 0.04 mm to 0.10 mm.

3. A stent with high radial force and bending flexibility, which has a generally tubular body formed of a plurality of ring units each formed of a plurality of ring units, and said tubular body is expandable in the radial direction of said tubular body from inside of said tubular body,
   each of the plurality of ring units being formed of a plurality of cells connected to one another circumferentially around a central axis (C1) of the stent forming said tubular body,
   said ring units being arranged in an axial direction along the central axis (C1) of the stent forming said tubular body such that adjacent ring units are connected to each other with connector portions, (i) each of said connector portions being generally S-shaped and formed of two arched portions, each arched portion having an arch of curvature radius R, and a generally linear portion therebetween, wherein each connector portion is connected to at least one cell of one of the plurality of ring units and at least one cell of an adjacent ring unit, (ii) wherein each of said cells has a first configuration comprising a bendable and expandable curved portion having acute angle X, a first strut comprising a generally linear portion having an axially disposed position that is substantially parallel to the central axis (C1) of the tubular bodied stent, and a second strut comprising at least one curved line portion and at least one generally linear portion, wherein the generally linear portion of the first strut is adjacent and continued with the bendable and expandable curved portion and the generally linear portion of the second strut is adjacent to and continued with the bendable and expandable curved portion, wherein a longitudinal axis of the first strut and a longitudinal axis of the generally linear portion of the second strut intersect to form the acute angle X of said bendable and expandable curved portion, (iii) wherein in the first configuration, the cells and the connector portions are so disposed such that there is at least one of a first space between each first strut and each adjacent second strut (Si), a second space between each bendable and expandable curved portion and each adjacent arched portion of each connector portion (Sii), and a third space between adjacent arched portions of adjacent connector portions (Siii), (iv) wherein when compression of the stent in the radial direction is made, each of said cells has a compressed configuration, wherein the first strut maintains the axially disposed position and the second strut bends toward said first strut, wherein, in the compressed configuration at least part of adjacent first and second struts make contact, and at least part of adjacent connector portions make contact, wherein when the stent is expanded until said tubular body has a diameter of 2.5 mm, the first strut and the second strut form an angle of at least 30° after expansion, wherein said cells are arranged circumferentially, 6 to 12 cells are arranged when the tubular body has a diameter of 3.0 mm or more after expansion of the stent, wherein said cells are arranged in the axial direction of the stent such that 3 to 8 cells are disposed per 10 mm of the length of said stent, wherein the ratio of the length of each cell in the axial direction of the stent and the length of each connector portion in the axial direction of the stent is 50 to 100, and wherein said stent with said cells in said compressed configuration is configured to be mounted on a balloon and transported in a blood vessel to a diseased part to be treated.

4. The stent as recited in claim 3, wherein said cells have a thickness of 0.06 mm to 0.12 mm and a width of 0.08 mm to 0.15 mm and said connector portions have a thickness of 0.06 to 0.12 mm and a width of 0.04 mm to 0.10 mm.

* * * * *